(12) United States Patent
Hale et al.

(10) Patent No.: US 9,254,137 B2
(45) Date of Patent: Feb. 9, 2016

(54) FACET IMPLANT

(75) Inventors: Horace Winston Hale, Degersheim (CH); Dieter Grob, Erlenbach (CH)

(73) Assignee: Lanterna Medical Technologies LTD, Watford (GB)

( * ) Notice: Subject to any disclaimer, the term of this patent is extended or adjusted under 35 U.S.C. 154(b) by 2400 days.

(21) Appl. No.: 10/651,871

(22) Filed: Aug. 29, 2003

(65) Prior Publication Data

US 2005/0049705 A1 Mar. 3, 2005

(51) Int. Cl.
*A61F 2/44* (2006.01)
*A61B 17/16* (2006.01)
*A61B 17/17* (2006.01)
*A61B 17/70* (2006.01)
*A61F 2/46* (2006.01)
*A61F 2/30* (2006.01)

(52) U.S. Cl.
CPC ......... *A61B 17/1671* (2013.01); *A61B 17/1757* (2013.01); *A61F 2/4405* (2013.01); *A61B 17/1659* (2013.01); *A61B 17/7064* (2013.01); *A61F 2/4611* (2013.01); *A61F 2002/3082* (2013.01); *A61F 2002/30405* (2013.01); *A61F 2002/30769* (2013.01); *A61F 2002/30841* (2013.01); *A61F 2002/30878* (2013.01); *A61F 2220/0025* (2013.01); *A61F 2310/00023* (2013.01); *A61F 2310/00029* (2013.01); *A61F 2310/00131* (2013.01); *A61F 2310/00161* (2013.01); *A61F 2310/00203* (2013.01); *A61F 2310/00239* (2013.01)

(58) Field of Classification Search
USPC ............................... 623/17.11–17.16; 606/61
See application file for complete search history.

(56) References Cited

U.S. PATENT DOCUMENTS

| | | | |
|---|---|---|---|
| 3,879,767 | A | 4/1975 | Stubstad |
| 4,001,896 | A | 1/1977 | Arkangel |
| 4,085,466 | A | 4/1978 | Goodfellow |
| 4,502,161 | A | 3/1985 | Wall |
| 4,714,469 | A | 12/1987 | Kenna |

(Continued)

FOREIGN PATENT DOCUMENTS

| | | |
|---|---|---|
| DE | 9304368 | 3/1993 |
| DE | 9304368.4 | 3/1993 |

(Continued)

OTHER PUBLICATIONS

Chiu, J.C., Davis, G.W., Clifford, T., and Greenspan M. Translaminar Facet Screw Fixation [retreived on May 27, 2003]. Retrieved from the Internet:<http://www.spinecenter.com/papers/facet/facet.htm.

(Continued)

*Primary Examiner* — Pedro Philogene
*Assistant Examiner* — David C Comstock
(74) *Attorney, Agent, or Firm* — Renner, Otto, Boisselle & Sklar, LLP

(57) ABSTRACT

Prostheses and methods for treating spinal pathologies and more specifically, for treating articulating surfaces of facet joints. The system includes a superior implant that is configured for placement on a superior articulating facet surface and an inferior implant that is configured for placement on an inferior articulating facet surface. The method includes creating a space between a superior and an inferior articular facet, such as by using a rasp, and fixing superior and inferior implants to the superior and inferior articular facets.

42 Claims, 7 Drawing Sheets

(56) References Cited

U.S. PATENT DOCUMENTS

| | | | |
|---|---|---|---|
| 4,759,766 A * | 7/1988 | Buettner-Janz et al. | 623/17.15 |
| 4,772,287 A | 9/1988 | Ray et al. | |
| 4,773,402 A | 9/1988 | Asher et al. | |
| 4,904,260 A | 2/1990 | Ray et al. | |
| 4,936,848 A | 6/1990 | Bagby | |
| 5,000,165 A | 3/1991 | Watanabe | |
| 5,127,912 A | 7/1992 | Ray et al. | |
| 5,360,431 A | 11/1994 | Puno et al. | |
| 5,527,314 A | 6/1996 | Brumfield et al. | |
| 5,571,191 A | 11/1996 | Fitz | |
| 5,586,989 A | 12/1996 | Bray, Jr. | |
| 5,591,165 A | 1/1997 | Jackson | |
| 5,683,466 A * | 11/1997 | Vitale | 623/21.15 |
| 5,895,428 A * | 4/1999 | Berry | 623/17.15 |
| 6,014,588 A | 1/2000 | Fitz | |
| 6,039,763 A * | 3/2000 | Shelokov | 623/17.16 |
| RE36,758 E | 6/2000 | Fitz | |
| 6,132,464 A | 10/2000 | Martin | |
| 6,379,386 B1 * | 4/2002 | Resch et al. | 623/19.13 |
| 6,436,101 B1 | 8/2002 | Hamada | |
| 6,565,605 B2 | 5/2003 | Goble et al. | |
| 6,579,319 B2 | 6/2003 | Goble et al. | |
| 6,610,091 B1 | 8/2003 | Reiley | |
| 6,706,068 B2 * | 3/2004 | Ferree | 623/17.11 |
| 6,810,567 B2 | 11/2004 | Reiley | |
| 6,908,484 B2 * | 6/2005 | Zubok et al. | 623/17.15 |
| 2002/0019637 A1 | 2/2002 | Frey et al. | |
| 2002/0123806 A1 | 9/2002 | Reiley | |
| 2002/0151895 A1 * | 10/2002 | Soboleski et al. | 606/61 |
| 2003/0004572 A1 | 1/2003 | Goble et al. | |
| 2003/0028250 A1 | 2/2003 | Reiley et al. | |
| 2003/0216669 A1 | 11/2003 | Lang et al. | |
| 2004/0024462 A1 * | 2/2004 | Ferree et al. | 623/17.14 |
| 2004/0176844 A1 * | 9/2004 | Zubok et al. | 623/17.15 |
| 2005/0143818 A1 * | 6/2005 | Yuan et al. | 623/17.11 |

FOREIGN PATENT DOCUMENTS

| | | |
|---|---|---|
| DE | 10135771 | 2/2003 |
| EP | 0 322 334 A1 | 6/1989 |
| EP | 0 392 124 A1 | 10/1990 |
| EP | 0 610 837 A1 | 8/1994 |
| WO | 93/14721 | 8/1993 |
| WO | 03/041618 A2 | 5/2003 |

OTHER PUBLICATIONS

Nabil A. Ebraheim, Rongming Xu, Eric Challgren, and Richard A. Yeasting, Journal of Spiral Disorders, "Quantitative Anatomy of the Cervical Facet and the Posterior Projection of Its Inferior Facet," vol. 10, No. 4, pp. 308-316, 1997.

Jan P.J. van Schaik and Bart van Pinxteren, Journal of Spinal Disorders, "Curvature of the Lower Lumbar Facet Joints: Variations at Different Levels and Relationship with Orientation," vol. 12, No. 4, pp. 341-347, 1999.

Jike Lu, M.D., Nabil A. Ebraheim, M.D., and Richard A. Yeasting, PhD, The American Journal of Orthopedics, "Translaminar Facet Screw Placement: an Anatomic Study," pp. 550-555, Aug. 1999.

Nabil A. Ebraheim, M.D., Rongming Xu, M.D., Huhammad Ahmad, M.D. and Richard A. Yeasting, PhD, "The Quantitative Anatomy of the Thoracic Facet and the Posterior Projection of Its Inferior Facet," Spine vol. 22, No. 16, pp. 1811-1818, 1997.

Manohar M. Panjabi, PhD, Thomas Oxland, MASc, Koichiro Takata, M.D., Vijay Goel, PhD, Joanne Duranceau, M.S. and Martin Krag, M.D., "Articular Facets of the Human Spine, Quantitative Three-Dimensional Anatomy," Spine vol. 18, No. 10, pp. 1298-1310, 1993.

Scott D. Boden, M.D., K. Daniel Riew, M.D., Ken Yamaguchi, M.D., Thomas P. Branch, M.D., Dieter Schellinger, M.D., and Sam W. Wiesel, Atlanta Georgia, "Orientation of the Lumbar Facet Joints: Association with Degenerative Disc Disease," The Journal of Bone and Joint Surgery, Inc., vol. 78-A, No. 3, Mar. 1996.

John M Cavanaugh, A. Cuneyt Ozaktay, H. Toshihiko Yamashita, and Albert I. King, "Lumbar Facet Pain: Biomechanics Neuroanatomy and Neurophysiology," Survey Article, J. Biomechanics, vol. 29, No. 9, pp. 1117-1129, 1996.

Dudley, Hugh A.F., ed., Carter, David C., ed. and Russell, R.C.G., ed., "Spinal Injuries," *Rod & Operative Surgery—Orthopaedics Part 1*, London: Butterworth-Heinemann, 1991, p. 641.

Office Action for corresponding Japanese Application No. 2006-524924 completed Nov. 24, 2009.

D. Grob et al., "Translaminar screw fixation in the lumbar spine; technique, indications, results", Apr. 6, 1998, Eur Spine J. (1998) 7:178-186.

Based on a Supplemental Search Report corresponding European Application No. 04782550.0 completed May 19, 2010.

\* cited by examiner

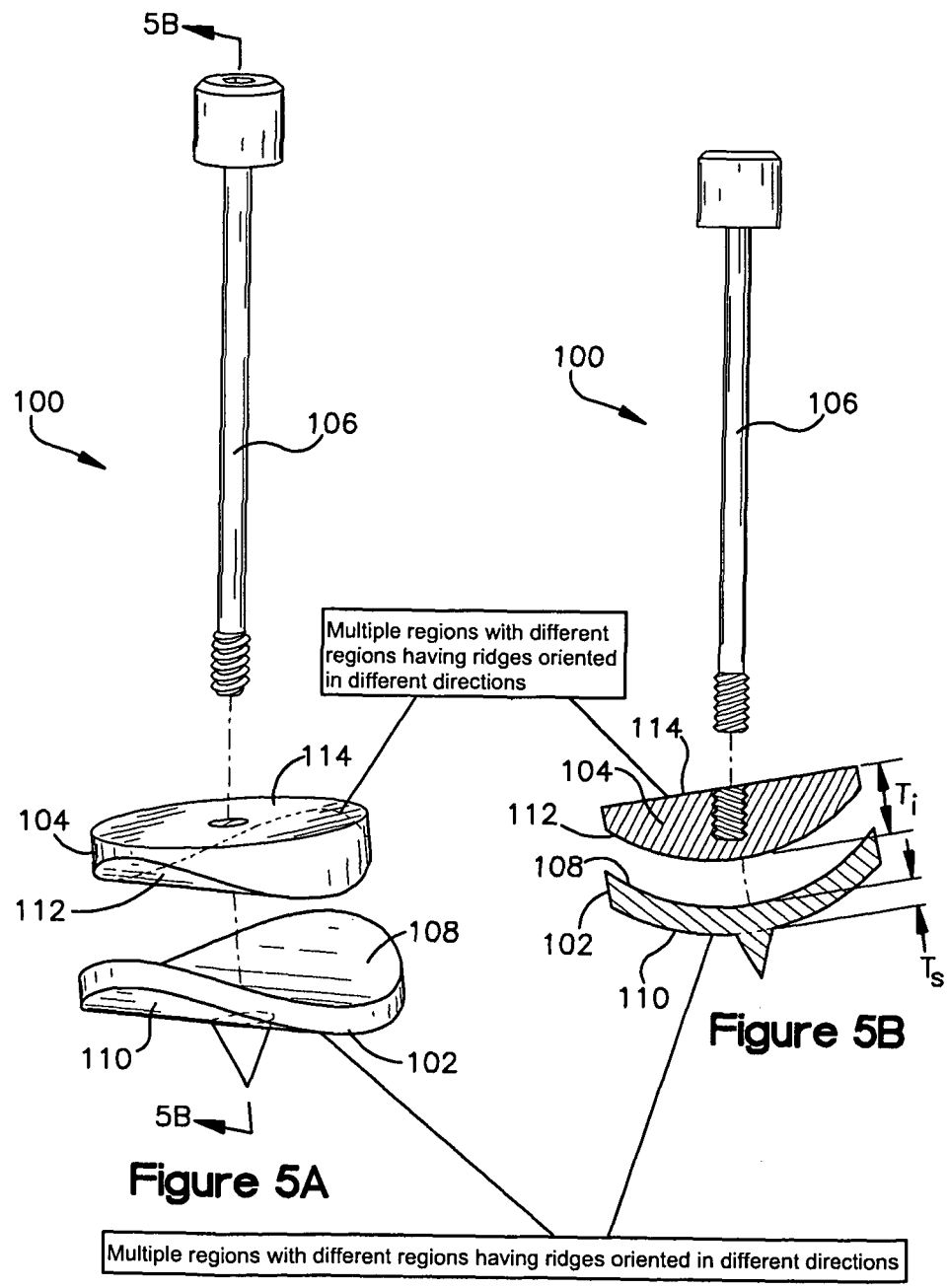

FACET IMPLANT

FIELD OF THE INVENTION

The present invention relates generally to prostheses for treating spinal pathologies, and more specifically to a system and method for treating articulating surfaces of facet joints.

BACKGROUND OF THE INVENTION

Back pain, such as in the "small of the back", or lumbosacral (L4-S1) region, is a common ailment. In many cases, the pain severely limits a person's functional ability and quality of life. A variety of spinal pathologies can lead to back pain.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort. With respect to vertebral articular surface degeneration, facet joints may show a reduced thickness of cartilage and may advance to entire disappearance thereof. Furthermore, surrounding the degenerated articular surfaces, there is bony formation able to give neurological compressions inside either the foramenae or spinal canal. These facts induce lower back and nerve roots pain which affect a large part of the population.

The vertebral facet joints, for example, can be damaged by either traumatic injury or by various disease processes, such as osteoarthritis, ankylosing spondylolysis, and degenerative spondylolisthesis. The damage to the facet joints often results in pressure on nerves, also called a "pinched" nerve, or nerve impingement. The result is pain, misaligned anatomy, and a corresponding loss of mobility. Pressure on nerves can also occur without facet joint pathology, e.g., a herniated disc.

Degenerative spinal diseases can involve articular surfaces only, but may also have a more invasive pathology including traumatic, infectious, tumorous or dysmorphic (spondylolisthesis, for example) effecting the destruction of all or part of the articular process. The locking of vertebral motions by spinal arthrodesis or ligamentoplasty induces, beyond a spinal stiffness, an increased force on the joint facets of the adjacent vertebrae above and below the fusion, usually sustained by the considered intervertebral space and therefore an increase of degeneration of these joint facets.

One type of conventional treatment of facet joint pathology is spinal stabilization, also known as intervertebral stabilization. By applying intervertebral stabilization, one can prevent relative motion between the vertebrae. By preventing this movement, pain can be reduced. Stabilization can be accomplished by various methods. One method of stabilization is spinal fusion. Another method of stabilization is fixation of any number of vertebrae to stabilize and prevent movement of the vertebrae. Yet another type of conventional treatment is decompressive laminectomy. This procedure involves excision of the laminae to relieve compression of nerves. With regard to discal prostheses, they provide a "space" between two vertebral bodies while preserving some motion. They solve the aging intervertebral disc problem but do not function to reduce the force on posterior joint facets.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit a person's mobility. Some procedures involving motion devices have a high incidence of spontaneous fusion. There is thus a need in the art for a system and procedure capable of increasing the percentage of good results in disc replacement surgery. In addition, there is a need in the art for better results than are commonly achieved through trans-articular fusions. Further, there is a need in the art for a system and procedure that permits greater mobility in cases of spinal problems involving only the facet joints, and for obviating the need for spinal fusion associated with degenerative and congenital problems of the spine.

BRIEF SUMMARY OF THE INVENTION

According to an aspect of the invention, a facet implant comprising: a superior implant having an articulating surface and a fixation surface and being configured for placement on a superior articular facet; a inferior implant having an articulating surface and a fixation surface and being configured for placement on an inferior articular facet and for interacting with a translaminar fixation mechanism, whereby the articulating surface of the superior implant and the articulating surface of the inferior implant are configured to interact; and a translaminar fixation mechanism for securing the inferior implant to the inferior articular facet.

According to another aspect of the invention, a facet implant comprises: a superior implant having a fixation surface and a generally curved articulating surface, the superior implant being configured for placement on a specifically prepared articulating surface of a superior articular facet; and an inferior implant having a fixation surface and a generally convex articulating surface, the inferior implant being configured for placement on a specifically prepared articulating surface of an inferior articular facet, whereby the generally curved articulating surface of the superior implant and the generally convex articulating surface of the inferior implant being configured to interact.

According to another aspect of the invention, a method for providing articulating surfaces for facet joint articular facets comprises: creating a space between a superior articular facet and an inferior articular facet; using a rasp to prepare the articulating surface of the inferior articular facet for an inferior implant; using a rasp to prepare the articulating surface of the superior articular facet for a superior implant; placing the inferior implant on the inferior articular facet such that an articulating surface of the inferior implant is positioned on the articulating surface of the inferior articular facet; placing the superior implant on the superior articular facet such that an articulating surface of the superior implant is positioned on the articulating surface of the superior articular facet; wherein the articulating surface of the superior implant and the articulating surface of the inferior implant are configured to articulate with one another.

According to another aspect of the invention, a facet implant comprises: a superior implant having a fixation surface and a generally curved articulating surface, the superior implant being configured for placement on a specifically prepared articulating surface of a superior articular facet; a inferior implant having a fixation surface and a generally convex articulating surface, the inferior implant being configured for placement on a specifically prepared articulating surface of an inferior articular facet and for interacting with a translaminar screw, whereby the articulating surface of the superior implant and the articulating surface of the inferior implant being configured to interact; and a translaminar fixation mechanism for securing the inferior implant to the inferior articular facet.

According to another aspect of the invention, a rasp for preparing an articulating surface of a facet joint articular facet for an implant comprises: at least one handle; a shaft connecting the at least one handle to a working end of the rasp; and a generally curved head at the working end of the rasp having at least one cutting surface configured to cut when the cutting surface is moved in a first direction, but not when the cutting surface is moved in a direction opposite of the first direction.

BRIEF DESCRIPTION OF THE DRAWINGS

FIGS. 5A-5C illustrate a facet implant alone and in conjunction with a facet joint in a posterior perspective view;

DETAILED DESCRIPTION OF THE INVENTION

Figure 1:
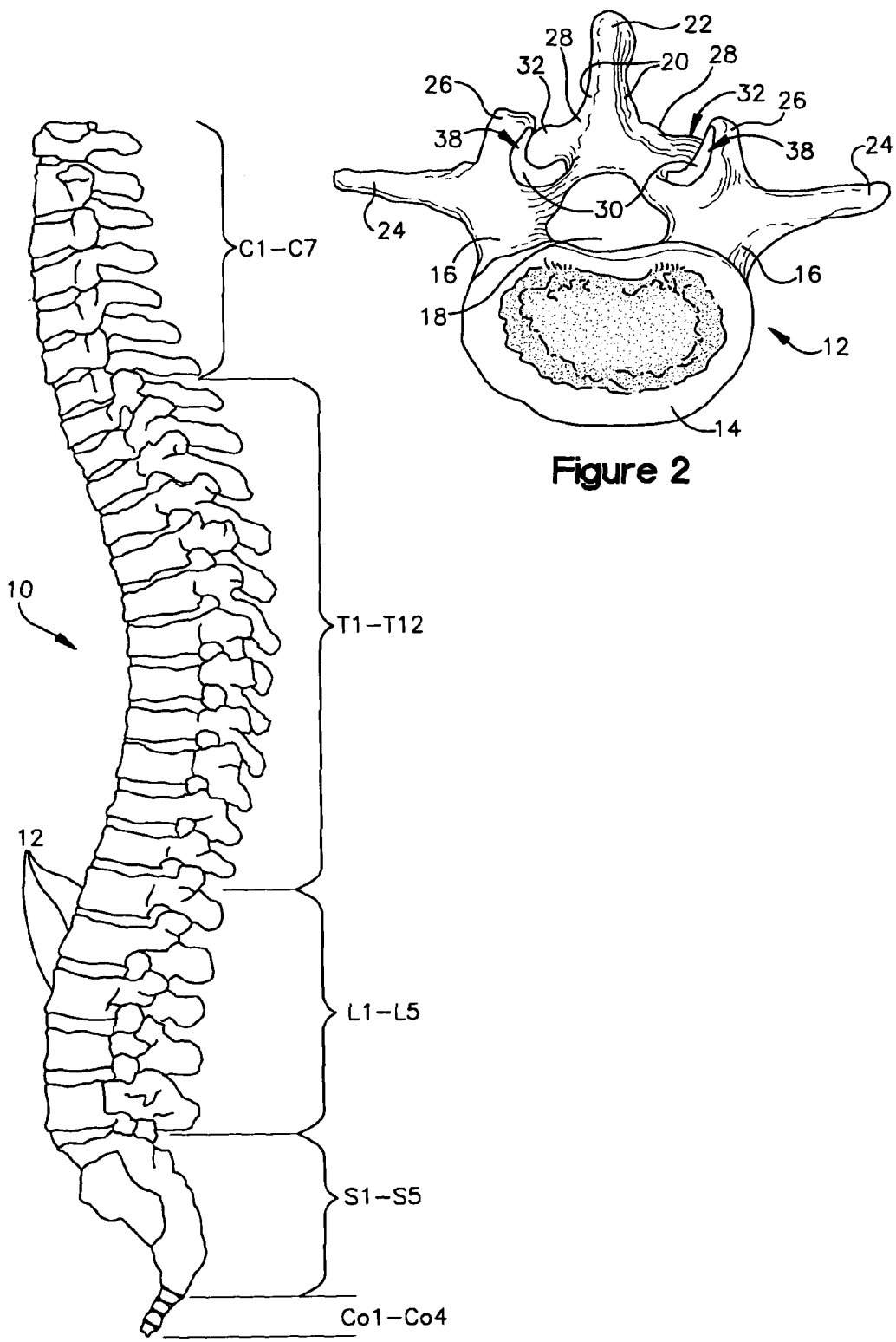
FIG. 1 is a lateral elevation view of a normal human spinal column.

Referring initially to FIG. 1, the human spinal column 10 is illustrated. The spinal column 10 is comprised of a series of thirty-three stacked vertebrae divided into five regions. The cervical region includes seven vertebrae, known as C1-C7. The thoracic region includes twelve vertebrae, known as T1-T12. The lumbar region contains five vertebrae, known as L1-L5. The sacral region is comprised of five vertebrae, known as S1-S5. The coccygeal region contains four vertebrae 12, known as Co1-Co4.

Figure 2:
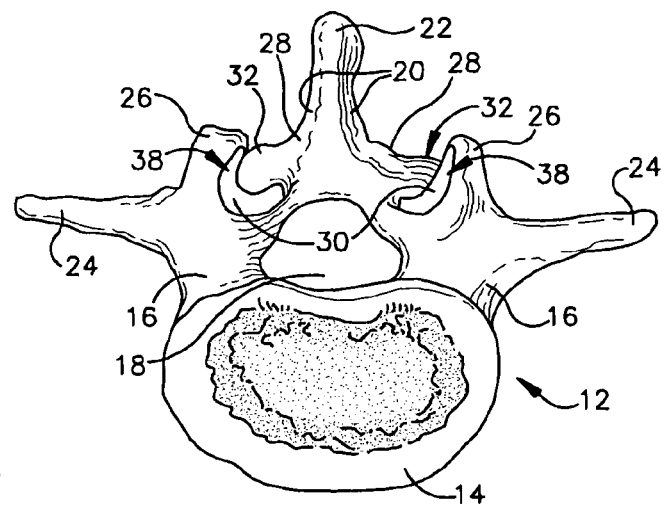
FIG. 2 is a superior view of a normal human lumbar vertebra.
Figure 3:
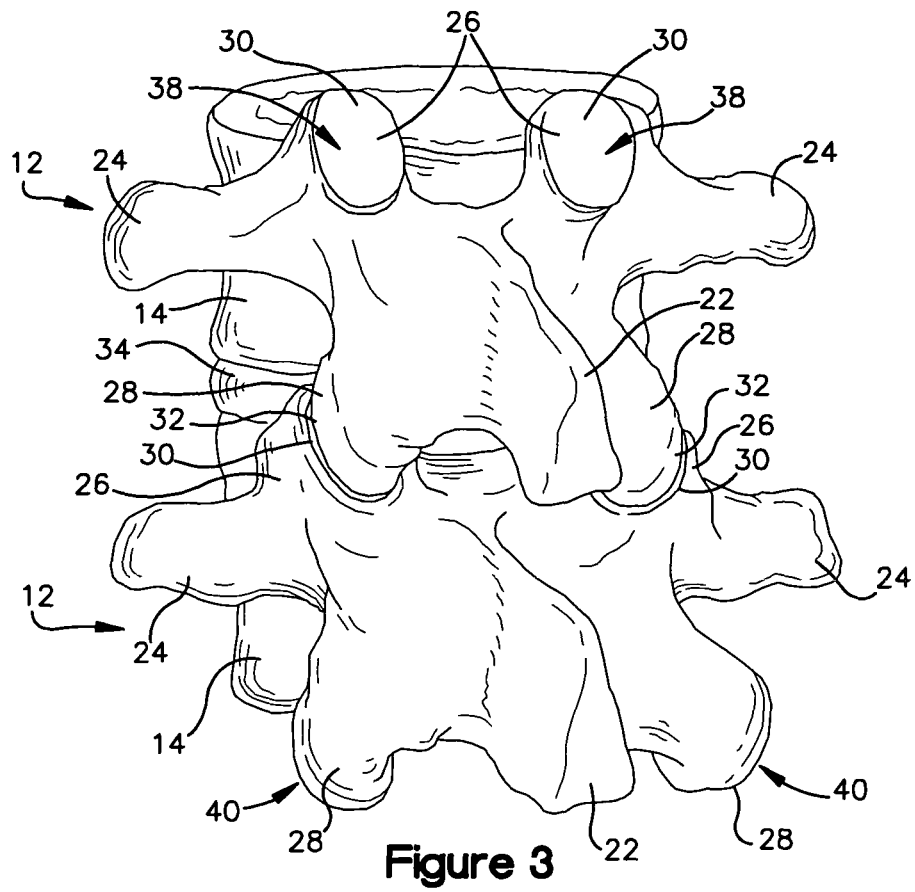
FIG. 3 is a posterior perspective view of a vertebral lumbar facet joint.

Turning now to FIGS. 2 and 3, normal human lumbar vertebrae 12 are illustrated. It will be understood by those skilled in the art that while the lumbar vertebrae 12 vary somewhat according to location, they share many features common to most vertebrae 12. Each vertebra 12 includes a vertebral body 14. Two short bones, the pedicles 16, extend backward from each side of the vertebral body 14 to form a vertebral arch 18. At the posterior end of each pedicle 16, the vertebral arch 18 flares out into broad plates of bone known as the laminae 20. The laminae 20 fuse with each other to form a spinous process 22. The spinous process 22 provides muscle and ligament attachment.

The transition from the pedicles 16 to the laminae 20 is interrupted by a series of processes. Two transverse processes 24 thrust out laterally on each side from the junction of the pedicle 16 and the lamina 20. The transverse processes 24 serve as guides for the attachment of muscles to the vertebrae 12. Four articular processes, two superior 26 and two inferior 28, also rise from the junctions of the pedicles 16 and the laminae 20. The superior articular processes 26 are oval plates of bone rising upward on each side from the union of the pedicle 16 with the lamina 20. The inferior processes 28 are oval plates of bone jutting downward on each side. The superior and inferior articular processes 26 and 28, respectively, each have a natural bony structure known as a facet. The superior articular facet 30 faces upward, while the inferior articular facet 32 faces downward. The superior articular facet 30 and the inferior articular facet 32 have articulating surfaces 38 and 40, respectively.

Figure 4:
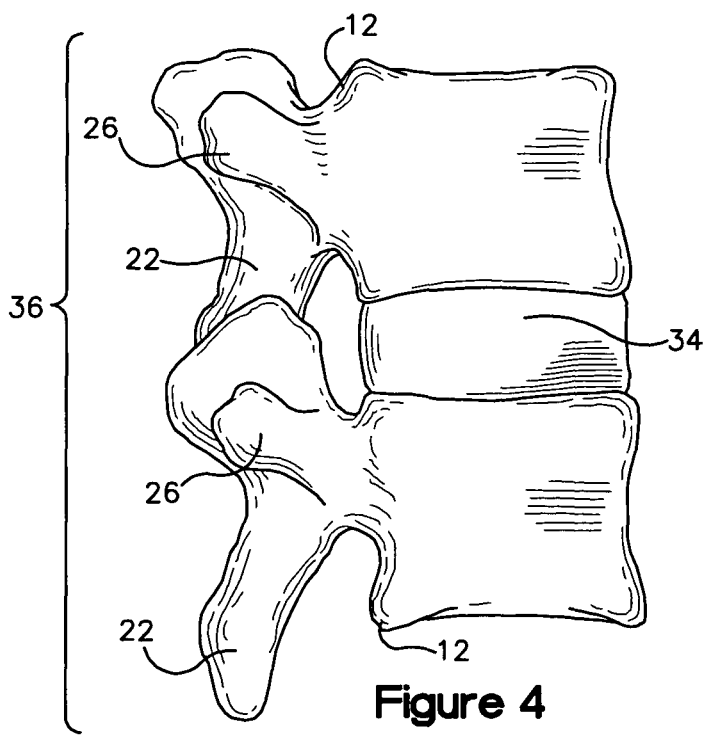
FIG. 4 is a lateral elevation view of a vertebral lumbar facet joint.

As shown in FIGS. 3 and 4, when adjacent vertebrae 12 are aligned, the superior articular facet 30 and inferior articular facet 32 interlock. Capped with a smooth articular cartilage, the interlocked vertebrae form a facet joint 36, also known as a zygapophysial joint. An intervertebral disc 34 between each pair of vertebrae 12 permits gliding movement between vertebrae 12. Thus, the structure and alignment of the vertebrae 12 permit a range of movement of the vertebrae 12 relative to each other.

The facet joint 36 is composed of a superior half and an inferior half. The superior half is formed by the vertebral level below the intervertebral disc 34, and the inferior half is formed by the vertebral level above the intervertebral disc 34. For example, in the L4-L5 facet joint, the superior portion of the joint is formed by bony structure on the L-5 vertebra (e.g., a superior articular surface and supporting bone on the L-5 vertebra), and the inferior portion of the joint is formed by bony structure on the L-4 vertebra (e.g., an inferior articular surface and supporting bone on the L-4 vertebra).

Figure 5C:
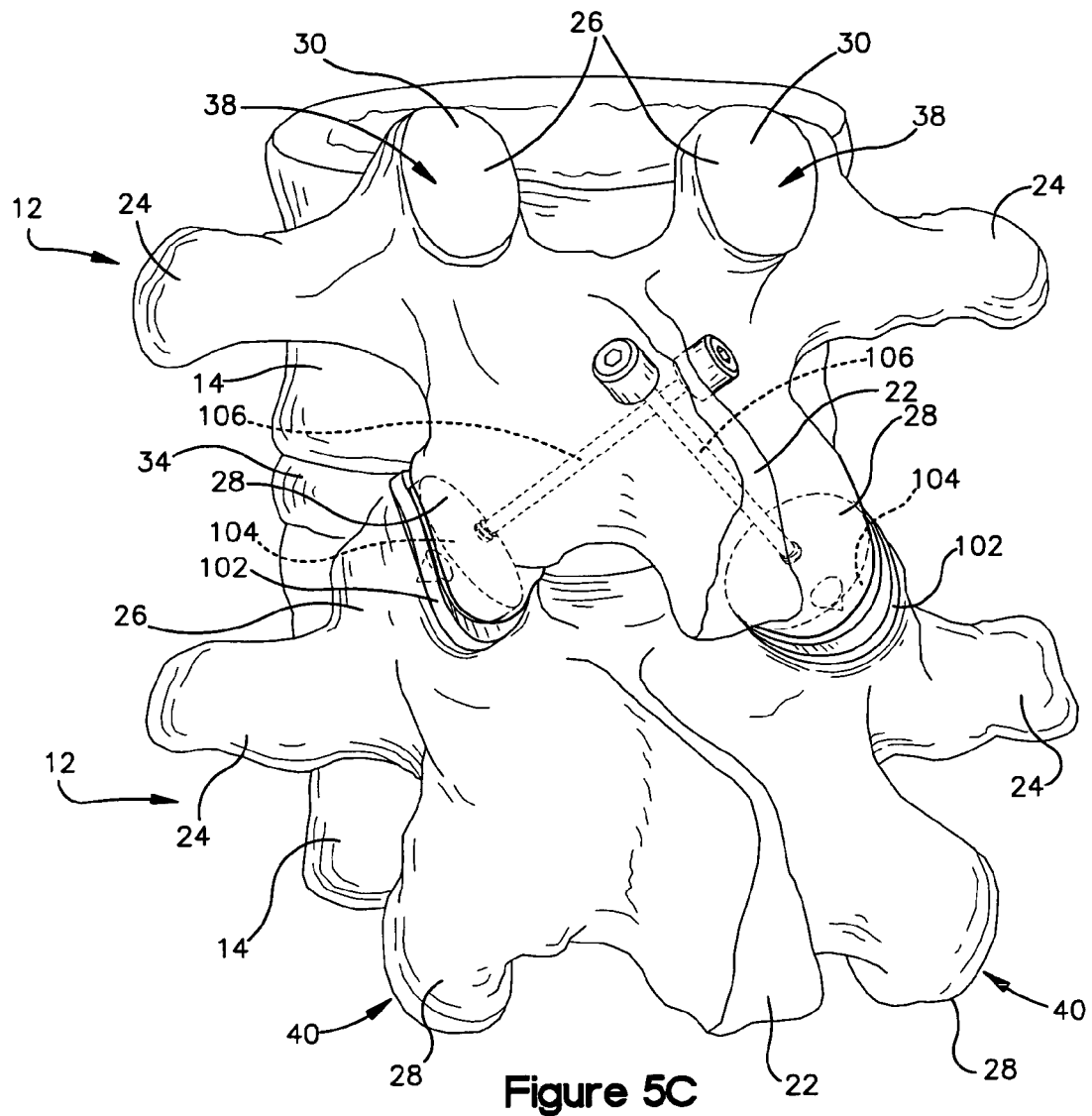

Turning now to FIGS. 5A and 5B, an exemplary facet implant according to the present invention is illustrated alone and in conjunction with a facet joint. The exemplary facet implant 100 generally has a superior implant 102 and an inferior implant 104. The superior implant 102 generally has an articulating surface 108 and a fixation surface 110. The inferior implant 104 generally has an articulating surface 112 and a fixation surface 114.

The superior implant 102 is configured for placement on superior articular facet 30. The superior implant 102 may be fixed to the superior articulating surface 38 using cemented and/or cementless fixation techniques. In an exemplary embodiment, the superior implant 102 has an articulating surface 108 and a fixation surface 110 and is configured for placement on a specifically prepared superior articulating surface 38. The articulating surface 108 may be generally curved and may be configured to interact with an articulating surface 112 of the inferior implant 104.

The superior implant 102 may have a surface fixation mechanism for fixing the superior implant 102, such as by fixing the fixation surface 110, to the superior articulating surface 38. The surface fixation mechanism may be any fixation mechanism known in the art, such as: one or more pegs, one or more pips, ridges or grooves, one or more screws. In an exemplary embodiment, the surface fixation mechanism includes a plurality of ridges, grouped in regions such that the ridges in different regions are oriented in different directions. For example, the surface fixation mechanism may include four regions on the fixation surface 110 where each of the four regions has ridges oriented in a different direction. The various orientations of the ridges prevent the superior implant 102 from moving in different directions with respect to the superior articulating surface 38.

The fixation surface 110 of the superior implant 102 may also have a porous coating; a porous onlay material; a biologic coating; a surface treatment, such as to facilitate bone ingrowth or cement fixation; and combinations thereof. For example, the fixation surface 110 may have a porous surface that is beaded, threaded, textured, etc. Further, the fixation surface 110 may have a hydroxyapatite coating or may be plasma-sprayed. In addition to the examples listed, any known method of improving fixation of biologic implants may be used to improve the interaction of the fixation surface 110 and the superior articular facet 30.

In one exemplary embodiment, the fixation surface 110 of the superior implant 102 is configured to interact only with the superior articulating surface 38 and does not interact directly with any other aspect of the superior articular facet 30, the superior articular process 26, or even the facet joint 36. The fixation surface 110 of the superior implant 102 may be generally curved for improved interaction with the superior articulating surface 38.

The articulating surface 108 in one exemplary embodiment is generally configured to articulate or interact with the articulating surface 112 of the inferior implant 104. Accordingly, the articulating surface 108 of the superior implant 102 may be generally curved. The superior implant 102 articulating surface 108 may be configured such that it acts as a "female" surface wherein it is concave or configured to accept a "male" articulating surface 112 of an inferior implant 104. Conversely, the superior implant 102 articulating surface 108 may also be configured such that it acts as a "male" surface wherein it is convex or configured to be accepted by "female" articulating surface 112 of an inferior implant 104.

The superior implant 102 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, Tantalum, Carbon composite materials and combinations thereof. For example, the superior implant 102 may be generally composed of titanium, but have a UHMWPE articulating surface. Some materials are more appropriate for articulating surfaces and some more appropriate for fixation surfaces, but any materials known in the art for use with articulating and fixation surfaces can be used in the present invention. Such materials are commonly used in joint arthroplasty and the like.

The superior implant 102 may be from about 2 mm thick to about 15 mm thick. In an exemplary embodiment, the thickness ($T_s$) of the superior implant 102 ranges from about 6 mm to about 10 mm. In another exemplary embodiment, the thickness ($T_s$) of the superior implant 102 ranges from about 3 mm to about 5 mm.

The inferior implant 104 is configured for placement on inferior articular facet 32. The inferior implant 104 may be fixed to the inferior articulating surface 40 using cemented and/or cementless fixation techniques. In an exemplary embodiment, the inferior implant 104 has an articulating surface 112 and a fixation surface 114 and is configured for placement on a specifically prepared inferior articulating surface 40. The articulating surface 112 may be generally convex and may be configured to interact with an articulating surface 108 of the superior implant 102.

The inferior implant 104 may have a surface fixation mechanism for fixing the inferior implant 104, such as by fixing the fixation surface 110, to the inferior articulating surface 40. The surface fixation mechanism may be any fixation mechanism known in the art, such as: one or more pegs, ridges or grooves, one or more screws. In an exemplary embodiment, the surface fixation mechanism includes a plurality of ridges, grouped in regions such that the ridges in different regions are oriented in different directions. For example, the surface fixation mechanism may include four regions on the fixation surface 114 where each of the four regions has ridges oriented in a different direction. The various orientations of the ridges prevent the inferior implant 104 from moving in different directions with respect to the inferior articulating surface 40.

The fixation surface 114 of the inferior implant 104 may also have a porous coating; a porous onlay material; a biologic coating; a surface treatment, such as to facilitate bone ingrowth or cement fixation; and combinations thereof. For example, the fixation surface 114 may have a porous surface that is beaded, threaded, textured, etc. Further, the fixation surface 114 may have a hydroxyapatite coating or may be plasma-sprayed. In addition to the examples listed, any known method of improving fixation of biologic implants may be used to improve the interaction of the fixation surface 110 and the superior articular facet 30.

In one exemplary embodiment, the fixation surface 114 of the inferior implant 104 is configured to interact only with the inferior articulating surface 40 and does not interact directly with any other aspect of the inferior articular facet 32, the inferior articular process 28, or even the facet joint 36. The fixation surface 114 of the inferior implant 104 may be generally flat or generally curved for improved interaction with the inferior articulating surface 40.

In another exemplary embodiment, the inferior implant 104 is configured to interact with or attach to a translaminar fixation mechanism 106. For example, the inferior implant 104 may include a threaded hole either extending from or bored into the fixation surface 114 of the inferior implant 110. The manner in which the inferior implant 104 and the translaminar fixation mechanism 106 interact may vary with different anatomies. For example, it may be preferable to offset the translaminar screw 106 from the inferior implant 104 such that when the translaminar screw 106 and inferior implant 104 interact, the translaminar screw 106 is not perpendicular to the inferior implant 104. The translaminar screw 106 may range from about 0 degrees offset from perpendicular to about 20 degrees offset from perpendicular. In one exemplary embodiment, the translaminar screw 106 ranges from about 5 degrees offset from perpendicular to about 15 degrees offset from perpendicular. In another exemplary embodiment, the translaminar screw 106 is about 10 degrees offset from perpendicular.

The articulating surface 112 of the inferior implant 104 in one exemplary embodiment is generally configured to articulate or interact with the articulating surface 108 of the superior implant 102. Accordingly, the articulating surface 112 of the inferior implant 104 may be generally convex. The inferior implant 104 articulating surface 112 may be configured such that it acts as a "male" surface wherein it is convex or configured to be accepted by a "female" articulating surface 108 of a superior implant 102. Conversely, the inferior implant 104 articulating surface 112 may also be configured such that it acts as a "female" surface wherein it is configured to accept a "male" articulating surface 108 of a superior implant 102.

The inferior implant 104 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, and combinations thereof. For example, the inferior implant 104 may be generally composed of a ceramic material or a cobalt-chromium alloy. Some materials are more appropriate for articulating surfaces and some more appropriate for fixation surfaces, but any materials known in the art for use with articulating and fixation surfaces can be used in the present invention. Such materials are commonly used in joint arthroplasty and the like.

The inferior implant 104 may be from about 2 mm thick to about 15 mm thick. In an exemplary embodiment, the thickness ($T_i$) of the inferior implant 104 ranges from about 6 mm to about 12 mm. In another exemplary embodiment, the thickness ($T_i$) of the inferior implant 104 ranges from about 3 mm to about 5 mm.

One exemplary embodiment of the present invention includes a translaminar fixation mechanism 106 configured to interact with the inferior implant 104. The translaminar fixation mechanism 106 secures the inferior implant 104 to the inferior articular facet 32. The translaminar fixation mechanism may be any fixation mechanism known in the art, such as a translaminar screw. The translaminar fixation mechanism may be made from any material known in art for medical fixation devices. For example, the translaminar fixation mechanism may be made from titanium, titanium/aluminum/vanadium (Ti/Al/V) alloys, Tantalum, CrCo, ceramic, carbon or carbon composite materials.

Figure 6:
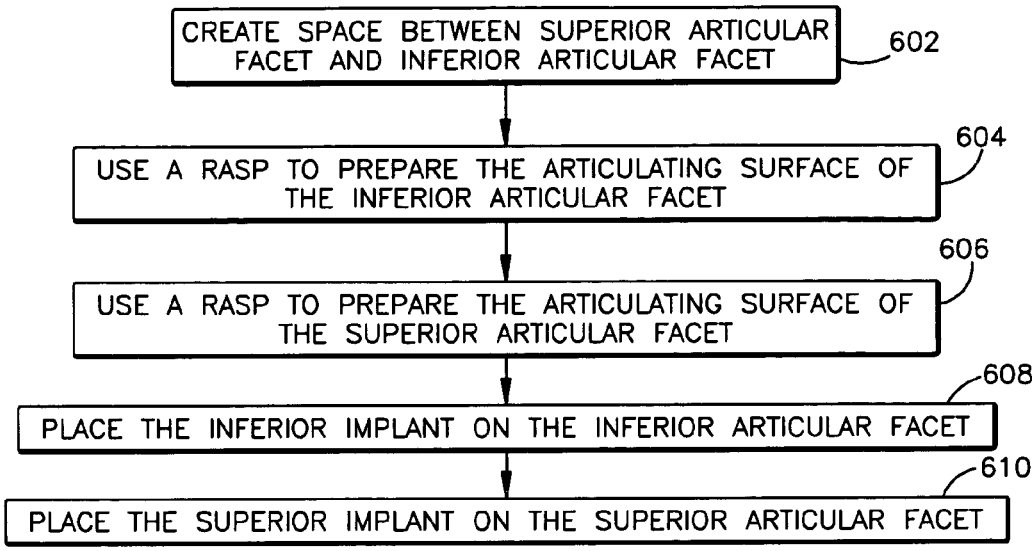
FIG. 6 is a flow chart generally illustrating a method for providing articulating surfaces for facet joint articular facets.

Turning next to FIG. 6, there is provided a flow diagram generally illustrating a method for providing articulating surfaces for facet joint articular facets. The overall flow begins at process block 602 wherein a space is created between the superior articular facet 30 and the inferior articular facet 32. It will be understood by those skilled in the art that prior to creating the space, it may be preferable or even necessary to expose the facet joint 36 at an effected level and remove the capsule. The effected level may be exposed through use of any appropriate procedure, such as a modified "Wiltse" approach. The creation of the space at process block 602 may be accomplished by using a curette or similar device and by removing the cartilaginous surfaces of the facet joint 36. In one exemplary embodiment, the created space is sufficient for using a rasp on an articulating surface of an articular facet. The space created between the superior articular facet 30 and the inferior articular facet 32 may range, for example, from about 2 mm to about 5 mm. In one exemplary embodiment, the space ranges from about 3 mm to about 4 mm.

Flow progresses to process block 604 wherein a rasp is used to prepare the articulating surface 40 of the inferior articular facet 32 for an inferior implant 104. Progression then continues to process block 606 wherein a rasp is used to prepare the articulating surface 38 of the superior articular facet 30 for a superior implant 102.

Figure 8:
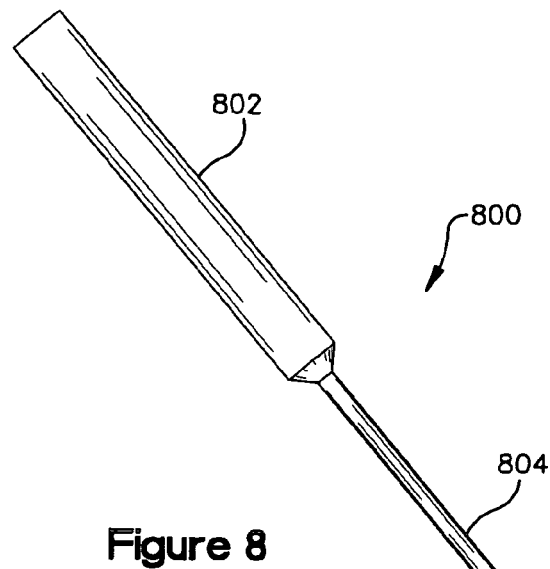
FIGS. 8-10 are illustrations of different types of rasps.
Figure 9:
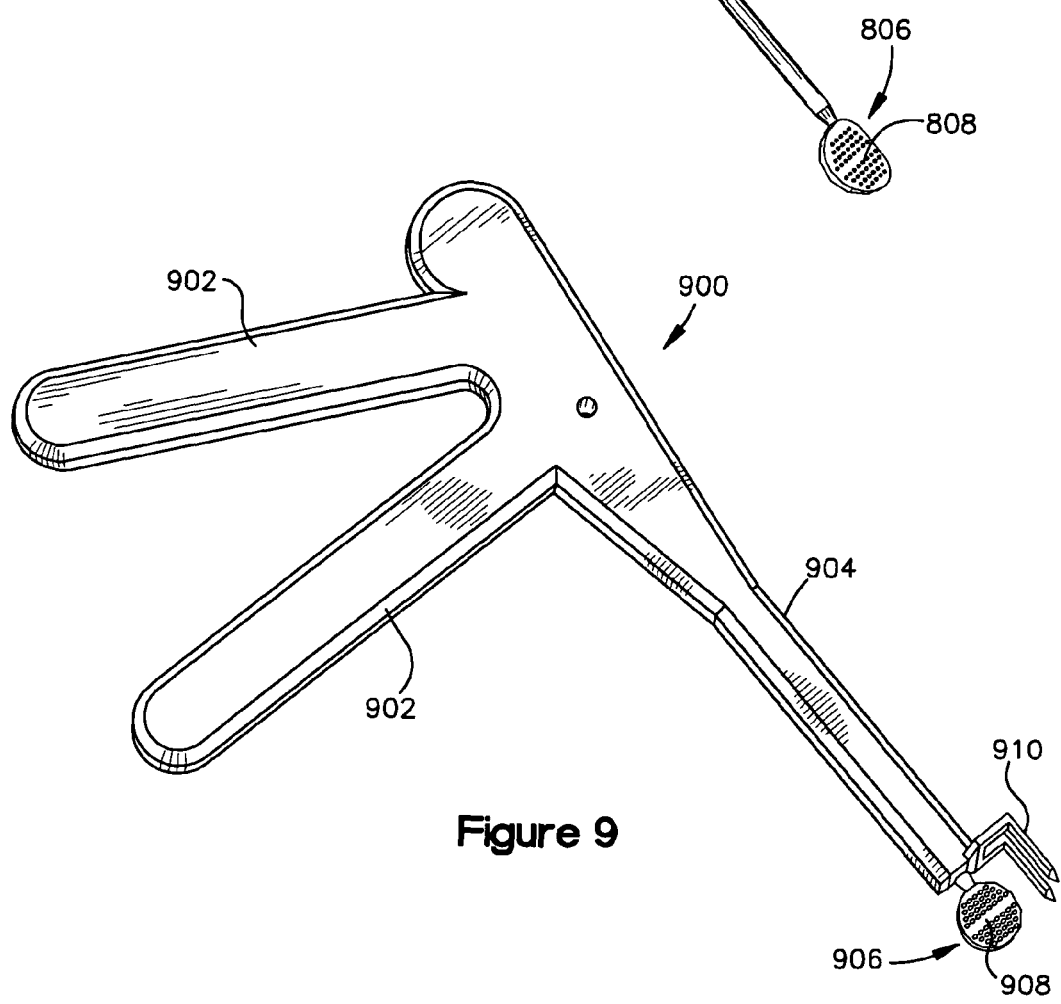
Figure 10:
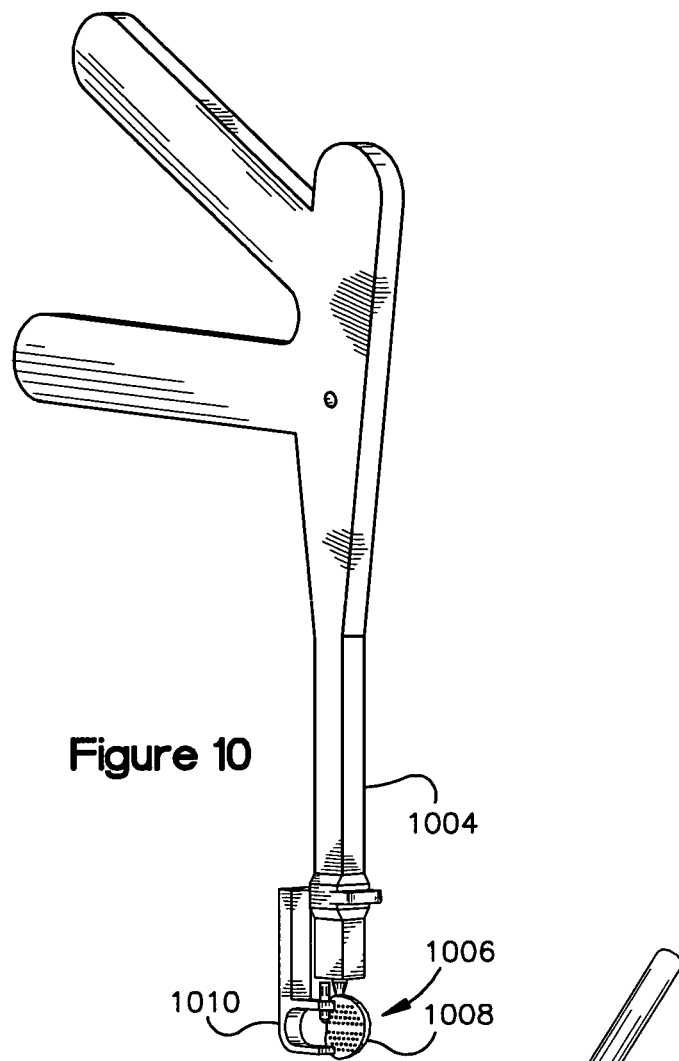

Each of the rasps of process blocks 604 and 606 may be either a single shaft rasp or a double action rasp, such as those illustrated in FIGS. 8-10 and described in detail herein. The process of preparing the articulating surfaces 38 and 40 of the articular facets 28 and 30 may involve using multiple rasps of increasing thickness while widening the space created in process block 602. For example, a 2 mm rasp may initially be used, then a 4 mm rasp, then a 6 mm rasp, then an 8 mm rasp, etc., until a desired result is achieved. In addition, the rasps of process blocks 604 and 606 may be the same rasp. Further, a single rasp can be used to prepare the articulating surfaces 38 and 40 concurrently. The articulating surfaces 38 and 40 may be prepared such that a bleeding bone bed is created to facilitate bone ingrowth for the superior implant 102 and inferior implant 104.

Figure 7:
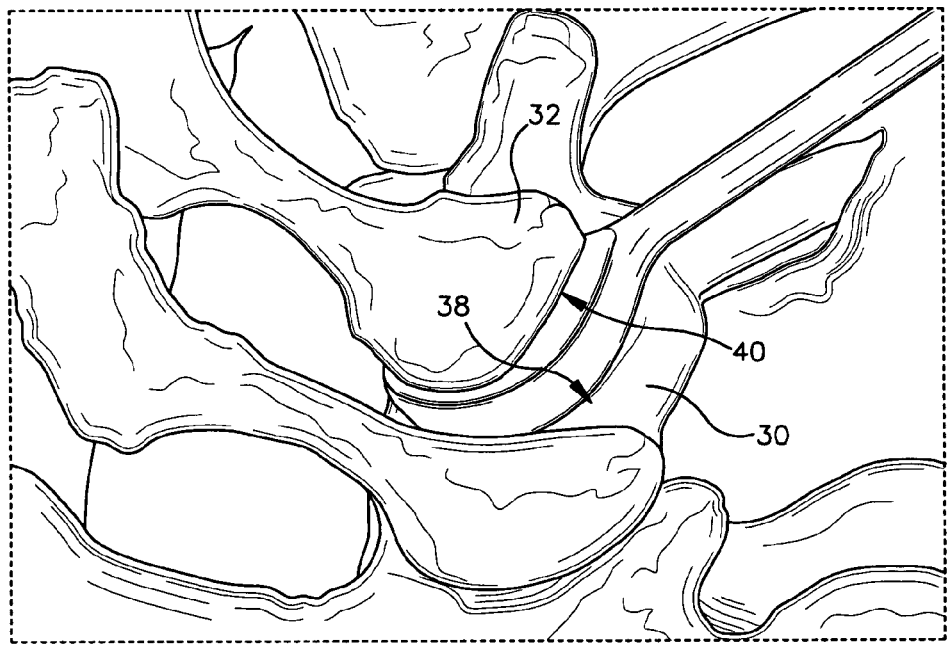
FIG. 7 is an illustration of a rasp being used to prepare an articulating surface.

As shown in FIG. 7, when the single handed rasp is used to prepare articulating surface 38 and/or articulating surface 40, the working end of the tool may be positioned inside the space created in process block 602. The rasp may then be moved from an anterior to a posterior position inside the facet joint 36 in order to effect a clean and uniform resection of the created space in the shape and dimension of both implants. In other words, the articulating surface 38 is prepared such that its shape and dimension resembles the superior implant 102 and the articulating surface 40 is prepared such that its shape and dimension resembles the inferior implant 104. The anterior/posterior movement of the rasp may be continued until the rasp is too small for the space created. The rasp may be too small when the space created is so wide that the rasp cannot prepare both the articulating surfaces 38 and 40 concurrently.

A larger (thicker) rasp may then be used. Increasingly larger rasps may be used until the created space is increased such that it ranges from about 4 mm to about 15 mm. In one exemplary embodiment, the rasps are designed to cut only when moving in a posterior direction to help prevent injury during the resurfacing process.

When a double action rasp is used, the working end of the rasp is positioned inside the created space and then the fixation appendages are secured to the lamina or to a cephalad position of the superior facet 26. The rasp is then moved in a cephalad/caudad direction by alternately squeezing and releasing the handles. Like the single handed rasp, double action rasp creates a clean and uniform resection of the created space in the shape and dimension of both implants. The alternately squeezing and releasing of the handles may be continued until the rasp is too small for the space created. The rasp may be too small when the space created is so wide that the rasp cannot prepare both the articulating surfaces 38 and 40 concurrently. A larger (thicker) rasp may then be used. Increasingly larger rasps may be used until the created space is increased such that it ranges from about 4 mm to about 15 mm. In one exemplary embodiment, the rasps are designed to cut only when moving in a caudad direction to help prevent injury during the resurfacing process.

In one embodiment, the steps of process blocks 602, 604 and 606 are repeated on the contralateral side of facet joint 36 prior to performing the steps of process block 608.

Progression then flows to process block 608 wherein the inferior implant 104 is placed on the prepared/resurfaced articulating surface 40 of the inferior articular facet 32. In one exemplary embodiment, the inferior implant 104 is placed such that it interacts with the articulating surface 40 of the inferior articular facet 32, but not with other aspects of the inferior articular facet 32.

In one exemplary embodiment, a translaminar screw 106 is used to secure the inferior implant 104 to the inferior articular facet 32. In this embodiment, the above method would also include using the translaminar screw 106 to secure the inferior implant 104 to the inferior articular facet 32. This exemplary embodiment preferably includes placing the translaminar screw 106 prior to placing the inferior implant 104 described in process block 608.

Figure 11:
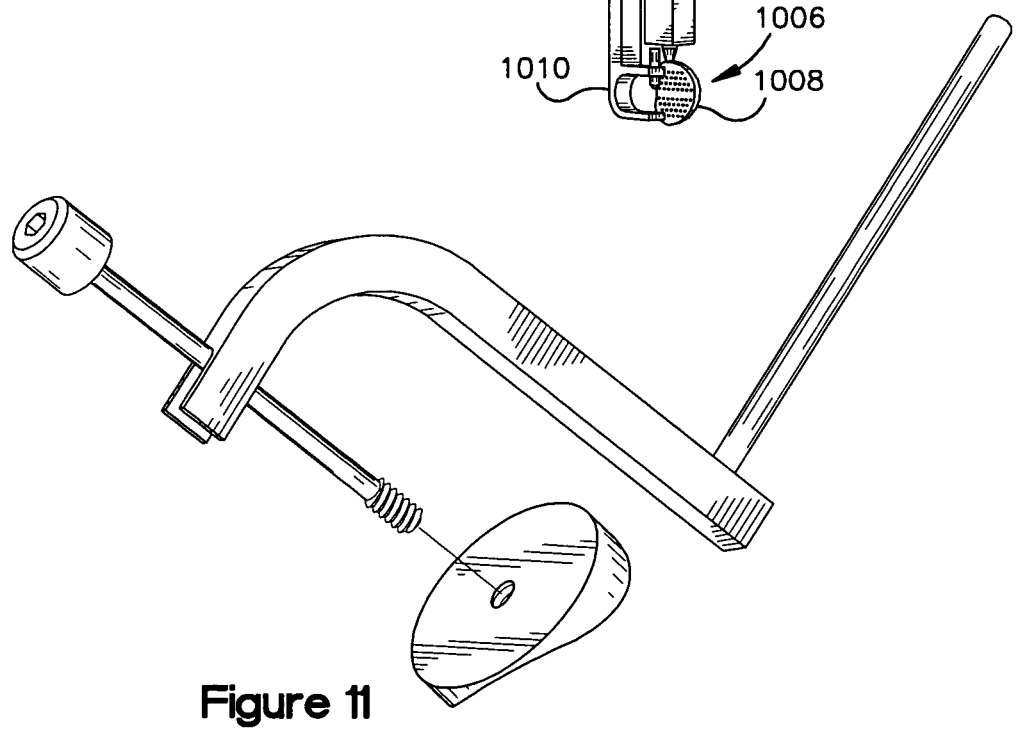
FIG. 11 is an illustration of an aiming device for use in positioning a translaminar screw.

To facilitate placement of the translaminar screw 106, an aiming device such as the one illustrated in FIG. 11 may be used. The aiming device can be used to position a drill for creating a translaminar hole for the translaminar screw 106. A drill can then be used to create the hole, which may have a diameter of about 2 mm, depending on the diameter of the translaminar screw 106. Once the hole is drilled, the translaminar screw 106 can be introduced into the hole and then used to secure the inferior implant 104 to the inferior articular facet 32.

In one embodiment, the steps of process blocks 608, including any steps associated with the drilling or placement of the translaminar screw 106, are repeated on the contralateral side of facet joint 36 prior to performing the steps of process block 610.

Progression then continues to process block 610 wherein the superior implant 102 is placed on the prepared/resurfaced articulating surface 38 of the superior articular facet 30. In one exemplary embodiment, the superior implant 102 is placed such that it interacts with the articulating surface 38 of the superior articular facet 30, but not with other aspects of the superior articular facet 30.

In one embodiment, the steps of process blocks 602, 604, 606, 608 and 610 are then repeated on the contralateral side.

Turning now to FIG. 8, a single handed rasp is illustrated. The rasp 800 includes a handle 802 and a shaft 804 connecting the handle 802 to the working end of the rasp 800. Attached to the shaft 804 at the working end of the rasp 800 is a head 806. The head 806 has at least one cutting surface 808. In one exemplary embodiment, the cutting surface 808 is configured to cut when the cutting surface 808 is moved in a first direction (e.g. when the rasp is moved from the anterior to the posterior direction of the facet joint) but not when the cutting surface 808 is moved in a direction opposite to the first direction (e.g. when the rasp is moved from the posterior to the anterior direction of the facet joint).

Turning now to FIG. 9, a double action rasp is illustrated. The rasp 900 includes two handles 902 and a shaft 904 connecting the handles 902 to the working end of the rasp 900. Attached to the shaft 904 at the working end of the rasp 900 are a head 906 and at least one fixation appendage 910. The head 906 has at least one cutting surface 908. In one exemplary embodiment, the cutting surface 908 is configured to cut when the cutting surface 908 is moved in a first direction (e.g. when the rasp is moved in a cephalad direction of the facet joint) but not when the cutting surface 908 is moved in a direction opposite to the first direction (e.g. when the rasp is moved in a caudad direction of the facet joint). In addition, the fixation appendages 910 may be configured for interaction with the lamina 20 or with a cephalad position of the superior facet 26. In one exemplary embodiment of a double action rasp 900, squeezing the handles 902 of the rasp 900 causes the head 906 to move in a cephalad position and releasing the handles 902 causes the head 906 to move in a caudad direction.

Turning now to FIG. 10, another double action rasp is illustrated. Attached to the shaft 1004 at the working end of the rasp 1000 are a head 1006 and a fixation appendage 1010. The fixation appendage 1010 may be rigid or capable of pivoting to accommodate various working angles. The head 1006 has at least one cutting surface 1008. In one exemplary embodiment, the cutting surface 1008 is configured to cut when the cutting surface 1008 is moved in a first direction but not when the cutting surface 1008 is moved in a direction opposite to the first direction. In one exemplary embodiment, the rasp is a double action rasp like the rasp 900 where squeezing the handles of the rasp causes the head 1006 to move in a first direction and releasing the handles causes the head 1006 to move in a second direction.

The rasps 800, 900 and 1000 of FIGS. 8-10 are configured to prepare the articulating surfaces of a facet joint. In an exemplary embodiment, the rasps 800, 900 and 1000 are configured to prepare articulating surfaces 38 and 40 of the articular facets 28 and 30 such that the shape and dimension of the prepared articulating surfaces resembles the shape and dimension of the superior implant 102 and inferior implant 104. For example, if the superior implant 102 and/or inferior implant 104 are curved, the head 806, 906 and 1006 may be generally curved to properly prepare the surface for the implant.

In addition, the rasps 800, 900 and 1000 may be made from any appropriate material commonly used for medical tools. In one exemplary embodiment, at least part of the rasps 800, 900 and 1000 are made from titanium, although the rasps could also be made from any material known in the art.

While the present invention has been described in association with several exemplary embodiments, the described embodiments are to be considered in all respects as illustrative and not restrictive. Such other features, aspects, variations, modifications, and substitution of equivalents may be made without departing from the spirit and scope of this invention which is intended to be limited solely by the scope of the following claims. Also, it will be appreciated that features and parts illustrated in one embodiment may be used, or may be applicable, in the same or in a similar way in other embodiments.

What is claimed is:

1. A facet implant comprising:
   a superior implant having an articulating surface and a fixation surface and being configured for placement on a superior articular facet of a vertebra of a human spine;
   an inferior implant having an articulating surface and a fixation surface and being configured for placement on an inferior articular facet of a vertebra of a human spine and for interacting with a translaminar fixation mechanism; and
   a translaminar fixation mechanism for securing the inferior implant to the inferior articular facet;
   wherein the articulating surface of the inferior implant and the articulating surface of the superior implant are configured to contact the other;
   wherein the entire area of the articulating surface of the inferior implant that contacts the articulating surface of the superior implant is generally smooth;
   wherein the entire area of the articulating surface of the superior implant that contacts the articulating surface of the inferior implant is generally smooth; and
   wherein the articulating surface of the inferior implant and the articulating surface of the superior implant are configured to articulate with the other in multiple directions while in contact with the other.

2. The facet implant of claim 1 wherein the translaminar fixation mechanism comprises at least one of: a translaminar screw, a bolt or a fixation pin.

3. The facet implant of claim 2 wherein the inferior implant is configured to interact with the translaminar fixation mechanism such that the translaminar fixation mechanism ranges from about 0 degrees to about 15 degrees offset.

4. The facet implant of claim 1 wherein at least one of the superior implant or the inferior implant comprises a surface fixation mechanism.

5. The facet implant of claim 4 wherein the surface fixation mechanism comprises at least one of: one or more pegs, one or more pips, ridges, or one or more screws.

6. The facet implant of claim 4 wherein the surface fixation mechanism comprises multiple regions wherein each of the regions has at least one ridge oriented in a different direction than the ridges of the other regions.

7. The facet implant of claim 1 wherein at least one of the fixation surfaces of the inferior implant and the superior implant has at least one of: a porous coating, a porous onlay material, a biologic coating, or a surface treatment.

8. The facet implant of claim 1 wherein the articulating surface of the superior implant is generally curved.

9. The facet implant of claim 1 wherein the fixation surface of the superior implant is generally curved.

10. The facet implant of claim 1 wherein the articulating surface of the inferior implant is generally curved.

11. The facet implant of claim 1 wherein at least one of the articulating surfaces of the inferior implant and the superior implant is composed of at least one of: cobalt-chromium alloy, ceramic, UHMWPE, pyrolytic carbon, or Ti/Al/V.

12. The facet implant of claim 1 wherein the inferior implant ranges from about 2 mm thick to about 15 mm thick.

13. The facet implant of claim 1 wherein the superior implant ranges from about 2 mm thick to about 15 mm thick.

14. The facet implant of claim 1 wherein the translaminar fixation mechanism is configured to traverse a lamina connected to the inferior articular facet.

15. A facet implant comprising:
a superior implant having a fixation surface and a generally curved articulating surface, the superior implant being configured for placement on a resurfaced articulating surface of a superior articular facet of a vertebra of a human spine; and
an inferior implant having a fixation surface and a generally convex articulating surface, the inferior implant being configured for placement on a resurfaced articulating surface of an inferior articular facet of a vertebra of a human spine;
wherein the articulating surface of the inferior implant and the articulating surface of the superior implant are configured to contact the other;
wherein the entire area of the articulating surface of the inferior implant that contacts the articulating surface of the superior implant is generally smooth;
wherein the entire area of the articulating surface of the superior implant that contacts the articulating surface of the inferior implant is generally smooth; and
wherein the articulating surface of the inferior implant and the articulating surface of the superior implant are configured to articulate with the other in multiple directions while in contact with the other.

16. The facet implant of claim 15 wherein at least one of the superior implant and the inferior implant comprises a surface fixation mechanism.

17. The facet implant of claim 16 wherein the surface fixation mechanism comprises at least one of: one or more pegs, one or more pips, ridges, or one or more screws.

18. The facet implant of claim 16 wherein the surface fixation mechanism comprises multiple regions wherein each of the regions has at least one ridge oriented in a different direction than the ridges of the other regions.

19. The facet implant of claim 15 wherein at least one of the fixation surfaces of the inferior implant and the superior implant has at least one of: a porous coating, a porous onlay material, a biologic coating, or a surface treated to facilitate bone ingrowth.

20. The facet implant of claim 15 wherein at least one of the articulating surfaces of the inferior implant and the superior implant is composed of at least one of: cobalt-chromium alloy, ceramic, UHMWPE, pyrolytic carbon, or Ti/Al/V.

21. The facet implant of claim 15 wherein the inferior implant is configured to engage a translaminar fixation mechanism that traverses a lamina connected to the inferior articular facet.

22. A facet implant comprising:
a superior implant having a fixation surface and a generally curved articulating surface, the superior implant being configured for placement on a resurfaced articulating surface of a superior articular facet of a vertebra of a human spine;
an inferior implant having a fixation surface and a generally convex articulating surface, the inferior implant being configured for placement on a resurfaced articulating surface of an inferior articular facet of a vertebra of a human spine and for interacting with a translaminar screw; and
a translaminar fixation mechanism adapted to secure the inferior implant to the inferior articular facet and to bone on the side of the spinous process of the vertebra opposite the inferior implant via a lamina adjacent to the inferior articular facet.

23. The facet implant of claim 22 wherein the translaminar fixation mechanism is configured to traverse a lamina connected to the inferior articular facet.

24. A facet implant comprising:
superior means for providing an artificial articulating surface on a superior articular facet of a vertebra of a human spine;
inferior means for providing an artificial articulating surface on an inferior articular facet of a vertebra of a human spine that is configured for multiple direction articulation when in contact with the artificial articulating surface on the superior articular facet; and
means for securing the inferior means to the inferior articular facet and to bone on the side of the spinous process of the vertebra opposite the inferior means via a lamina adjacent the inferior articular facet.

25. The facet implant of claim 24 wherein the means for securing the inferior means to the inferior articular facet comprises at least one of: a screw, a bolt or a fixation pin.

26. The facet implant of claim 24 wherein at least one of the superior means or the inferior means comprises a surface fixation mechanism.

27. The facet implant of claim 26 wherein the surface fixation mechanism comprises at least one of: one or more pegs, one or more pips, ridges, or one or more screws.

28. The facet implant of claim 24 wherein at least one of the superior means or the inferior means comprises a fixation surface having at least one of: a porous coating, a porous onlay material, a biologic coating, or a surface treatment.

29. The facet implant of claim 24 wherein at least one of the superior means or the inferior means comprises an articulating surface composed of at least one of: cobalt-chromium alloy, ceramic, UHMWPE, pyrolytic carbon, or Ti/Al/V.

30. A facet implant comprising:
superior means for providing an artificial articulating surface on a superior articular facet of a vertebra of a human spine, the superior means having a fixation surface and an articulating surface, the superior means being configured for placement on a resurfaced articulating surface of a superior articular facet such that the superior means primarily contacts only the articulating surface of the superior articulating facet; and
inferior means for providing an artificial articulating surface on an inferior articulating facet of a vertebra of a human spine that is configured for multiple direction articulation with the artificial articulating surface on the superior articular facet, the inferior means having a fixation surface and an articulating surface, the inferior means being configured for placement on a resurfaced articulating surface of an inferior articular facet such that the inferior means primarily contacts only the articulating surface of the inferior articulating facet;
wherein the generally curved artificial articulating surface of the superior articular facet and the generally convex artificial articulating surface of the inferior articular facet are configured for articulation in multiple directions while the artificial articulating surface of the superior articular facet and the artificial articulating surface of the inferior articular facet contact with one another;
wherein the entire area of the artificial articulating surface on the superior articular facet that contacts the artificial articulating surface on the inferior articular facet is generally smooth; and
wherein the entire area of the artificial articulating surface on the inferior articular facet that contacts the artificial articulating surface on the superior articular facet is generally smooth.

31. The facet implant of claim 30 wherein at least one of superior means or the inferior means comprises a surface fixation mechanism.

32. The facet implant of claim 31 wherein the surface fixation mechanism comprises at least one of: one or more pegs, one or more pips, ridges, or one or more screws.

33. The facet implant of claim 30 wherein at least one of the superior means or the inferior means comprises a fixation surface having at least one of: a porous coating, a porous onlay material, a biologic coating, or a surface treatment.

34. The facet implant of claim 30 wherein at least one of the superior means or the inferior means comprises an articulating surface composed of at least one of: cobalt-chromium alloy, ceramic, UHMWPE, pyrolytic carbon, or Ti/Al/V.

35. The facet implant of claim 30 further comprising means for securing the inferior means to the inferior articular facet via a lamina connected to the inferior articular facet.

36. A facet implant comprising:
a superior implant for providing an artificial articulating surface on a superior articular facet of a vertebra of a human spine, the superior implant having a fixation surface and an articulating surface, the superior implant being configured for placement on a specifically prepared articulating surface of a superior articular facet such that the superior implant primarily contacts only the articulating surface of the superior articulating facet; and
an inferior implant for providing an artificial articulating surface on an inferior articulating facet of a vertebra of a human spine that is configured for multiple direction articulation with the artificial articulating surface on the superior articular facet provided by the superior implant, the inferior means implant having a fixation surface and an articulating surface, the inferior implant being configured for placement on a specifically prepared articulating surface of an inferior articular facet such that the inferior implant primarily contacts only the articulating surface of the inferior articulating facet;
wherein the articulating surface of the superior implant and the articulating surface of the inferior implant are configured for articulation in multiple directions while the articulating surface of the superior implant contacts the articulating surface of the inferior implant;
wherein the entire area of the artificial articulating surface on the superior articular facet that contacts the artificial articulating surface on the inferior articular facet is generally smooth; and
wherein the entire area of the artificial articulating surface on the inferior articular facet that contacts the artificial articulating surface on the superior articular facet is generally smooth.

37. The facet implant of claim 36 wherein at least one of the superior implant or the inferior implant comprises a surface fixation mechanism.

38. The facet implant of claim 37 wherein the surface fixation mechanism comprises at least one of: one or more pegs, one or more pips, ridges, or one or more screws.

39. The facet implant of claim 36 wherein at least one of the superior implant or the inferior implant comprises a fixation surface having at least one of: a porous coating, a porous onlay material, a biologic coating, or a surface treatment.

40. The facet implant of claim 36 wherein at least one of the superior implant or the inferior implant comprises an articulating surface composed of at least one of: cobalt-chromium alloy, ceramic, UHMWPE, pyrolytic carbon, or Ti/Al/V.

41. The facet implant of claim 36 further comprising means for securing the inferior implant to the inferior articular facet via a lamina connected to the inferior articular facet.

42. A facet implant comprising:
a superior implant having an articulating surface and a fixation surface and being configured for placement on a superior articular facet of a vertebra of a human spine;
an inferior implant having an articulating surface and a fixation surface and being configured for placement on an inferior articular facet of a vertebra of a human spine and for interacting with a translaminar fixation mechanism; and
a fixation mechanism adapted to secure the inferior implant to the inferior articular facet by traversing a lamina connected to the inferior articular facet such that the inferior implant is secured to bone on the side of the spinous process of the vertebra opposite the inferior implant.

* * * * *